United States Patent
Athwal

(10) Patent No.: US 9,579,279 B2
(45) Date of Patent: Feb. 28, 2017

(54) SEAWEED-DERIVED COSMETIC COMPOSITIONS

(71) Applicant: Skinergistics Clinical Skin Solutions Inc., Vancouver (CA)

(72) Inventor: Gina Athwal, Vancouver (CA)

(73) Assignee: SKINERGISTICS CLINICAL SKIN SOLUTIONS INC., Vancouver (CA)

( * ) Notice: Subject to any disclaimer, the term of this patent is extended or adjusted under 35 U.S.C. 154(b) by 0 days.

(21) Appl. No.: 14/683,591

(22) Filed: Apr. 10, 2015

(65) Prior Publication Data

US 2016/0008267 A1    Jan. 14, 2016

Related U.S. Application Data

(63) Continuation of application No. 14/268,908, filed on May 2, 2014, now abandoned, which is a continuation of application No. 13/092,856, filed on Apr. 22, 2011, now abandoned.

(60) Provisional application No. 61/326,871, filed on Apr. 22, 2010.

(51) Int. Cl.
| | |
|---|---|
| *A61K 8/02* | (2006.01) |
| *A61K 8/97* | (2006.01) |
| *A61K 8/73* | (2006.01) |
| *A61Q 19/08* | (2006.01) |
| *A61Q 19/00* | (2006.01) |

(52) U.S. Cl.
CPC ............... *A61K 8/975* (2013.01); *A61K 8/73* (2013.01); *A61Q 19/00* (2013.01); *A61Q 19/08* (2013.01)

(58) Field of Classification Search
USPC ......................................................... 424/401
See application file for complete search history.

(56) References Cited

U.S. PATENT DOCUMENTS

| | | | |
|---|---|---|---|
| 5,158,772 A | 10/1992 | Davis | |
| 5,482,710 A | 1/1996 | Slavtcheff et al. | |
| 5,508,033 A | 4/1996 | Briand | |
| 6,410,062 B1 | 6/2002 | Callaghan et al. | |
| 6,433,025 B1* | 8/2002 | Lorenz | A61K 8/35 424/400 |
| 6,521,237 B2* | 2/2003 | Cole | A61K 8/365 424/400 |
| 7,025,966 B2 | 4/2006 | Majmudar | |
| 2002/0044915 A1 | 4/2002 | Lee et al. | |
| 2003/0039670 A1 | 2/2003 | Mizutani et al. | |
| 2004/0081675 A1* | 4/2004 | Wirth | A23L 1/3002 424/401 |
| 2004/0219124 A1 | 11/2004 | Gupta | |
| 2006/0275243 A1 | 12/2006 | Blume et al. | |
| 2007/0009455 A1* | 1/2007 | Kim | A61K 8/347 424/62 |
| 2007/0202496 A1* | 8/2007 | Beretta | G01N 33/57438 435/5 |
| 2007/0248563 A1* | 10/2007 | Iovanni | A61K 8/46 424/74 |
| 2008/0095731 A1* | 4/2008 | Mitra | A61K 8/60 424/70.13 |
| 2011/0243945 A1 | 10/2011 | Raats et al. | |
| 2011/0262505 A1 | 10/2011 | Athwal | |
| 2014/0242130 A1 | 8/2014 | Athwal | |

FOREIGN PATENT DOCUMENTS

| | | |
|---|---|---|
| EP | 0275005 B1 | 8/1993 |
| WO | WO-0166076 A2 | 9/2001 |
| WO | WO-2004100889 A2 | 11/2004 |
| WO | WO-2009147201 A2 | 12/2009 |

OTHER PUBLICATIONS

Hayden (Eur. J. Phycol. (Aug. 2003), 38: 277-294).*
Greenbaum et al. (Genome Biology, 2003, vol. 4, Issue 9, pp. 117.1-117.8).*
Liu et al. (Genome Biology 2009 10:R26).*
Aloecorp., Aloe Vera Science 2008.
Buyderm., http://www.buyderm.com/ingredients/soybeanProtein.asp, Jun. 28, 2007.
Dal'Belo., Skin Research and Technology 2006; 12: 241-246.
Eastman., http://www.cosmeticsdesign.com/Formulation-Science/Eastman-explains-benefit-of-vitamin-E-tocotrienols, Oct. 4, 2005.
Fitton., Cosmetics & Toiletries, vol. 122, No. 8 Aug. 2007 pp. 55-64.
Fuji., http://www.absolute-health.org/download/Fuji-Astaxanthin-for-Cosmetic-&-Personal-Care.pdf, 2006.
Ganoskin., http://www.ganoksin.com/borisat/nenam/pearl-skin-care.htm, 2005.
Induchem., "http://www.in-cosmetics.com/novadocuments/2570, Dec. 1, 2007."
Kawada., Journal of Dermatology 2008; 35: 637-642.
MMS., https://www.thesage.com/catalog/products/Allantoin.html, Jun. 10, 2008.
Office action dated Oct. 14, 2014 for U.S. Appl. No. 14/268,908.
OU., J Sci Food Agric 84:1261-1269; 2004.
Realself., http://www.realself.com/blog/armani-antiaging-skin-care-cream.html; Feb. 4, 2007.
Rinaudo., Prog. Polym. Sci. 31 (2006) 603-632.
Sephora., http://answers.sephora.com/answers/8723/product/P140620/questions.htm; Sep. 2009.
Specialchem., http://www.specialchem4cosmetics.com/services/inci/ingredient.aspx?id=12473; Mar. 17, 2009.
Tapp., http://forum.t-tapp.com/archive/index.php/t-862.html; Jun. 28, 1999.
Thibodeau., "(2005). Protecting the skin from environmental stresses with an exopolysaccharide formulation. Cosmetics and toiletries, 120(12), 81."
Tropolactive., http://www.tropolactive.com/pages/ingredients; Aug. 22, 2009.
Yoo., J. Cosmet Sci., 53, 175-184 (May/Jun. 2002).

* cited by examiner

*Primary Examiner* — Devang Thakor
(74) *Attorney, Agent, or Firm* — Snell & Wilmer LLP

(57) ABSTRACT

A cosmetic composition is disclosed for applying to skin. The composition includes a liquid and dispersed in the liquid: any amount or form of fucoidan, any amount or form of beta glucan; and any amount of a marine extract. When the cosmetic composition is applied to the skin, the appearance of the skin is improved.

21 Claims, No Drawings

SEAWEED-DERIVED COSMETIC COMPOSITIONS

CROSS-REFERENCE TO RELATED APPLICATIONS

This application is a continuation application of U.S. patent application Ser. No. 14/268,908, filed May 2, 2014, which is a continuation application of U.S. patent application Ser. No. 13/092,856, filed Apr. 22, 2011, which claims priority to U.S. Provisional Application No. 61/326,871 filed Apr. 22, 2010 which are hereby incorporated by reference for all purposes.

BACKGROUND OF THE INVENTION

I. Field of Invention

The present invention relates generally to a cosmetic composition and more particularly to a cosmetic composition containing seaweed for application to skin to improve the appearance of the skin.

II. Description of Related Art

The skin is one of the largest organs in the body. Skin is comprised of three main layers: the epidermis, the dermis and subcutaneous layers. At the outermost part of the epidermis, a layer of dead cells forms what is known as a stratum corneum layer. The dermis is the middle layer of skin and is comprised of arrangements of collagen fibres, which surround many specialized cells and structures. The innermost layer of the skin is the subcutaneous layer, often called the sub-dermis. The subcutaneous layer is comprised largely of fat and connective tissue and houses larger blood vessels and nerves. Elastin may be found in all layers of the skin, but is most prominent in the dermis layer.

The condition and appearance is a major concern to most people. Enhancing the appearance of the skin is of significant interest for many people. The appearance of the skin can be affected by many sources including environmental conditions such as sun exposure, building heating and air conditioning, and air pollution can accelerate deterioration of the condition and appearance of skin. Additionally, certain diseases can affect the appearance of the skin. Deterioration of the appearance of the skin may include, but is not limited to, wrinkles, loss of firmness and elasticity of the skin, age spots, discolorations, and dryness. In addition, individual factors such as diet, stress, age and genetics may affect the appearance of the skin.

Various compositions and methods for manipulating the appearance of the skin have been reported. For example, international patent application, published under number WO/2004/100889, describes anti-ageing agents, including 3,3'-thiodipropionic acid or derivatives thereof for improving the aesthetic appearance of skin. Another method of manipulating the quality of the skin is cosmetic surgery. It has been reported that seaweed extracts can be incorporated in compositions for use on the skin (see, for e.g., United States patent application 2004/0219124).

SUMMARY OF THE INVENTION

In accordance with one aspect of the invention there is provided a cosmetic composition for applying to skin. The composition includes a liquid, and dispersed in the liquid any amount of fucoidan, any amount of beta glucan, and any amount of a marine extract, wherein the cosmetic composition improves the appearance of the skin to which the composition is applied.

The composition may further include water as the liquid. The composition may further include the liquid being a glycolic acid-salicylic acid solution. The composition may further include the liquid being water and a glycolic acid-salicylic acid solution. The composition may further include the marine extract being any one or more of a green seaweed, a brown seaweed, an exopolysaccharide, or an algae. The composition may further include the marine extract being *Ulva lactuta, Alteromonas maclodeii,* Astaxanthin, or *Ecklonia cava.*

In another aspect of the invention, the composition may include any amount of tourmaline. In another aspect of the invention, the composition may include any amount of volcanic obsidian. In another aspect of the invention, the composition may include any amount of *Aloe barbadensis.* In another aspect of the invention, the composition may include any amount of hydrolyzed pearl nacre. In another aspect of the invention, the composition may include any amount of chitosan. In another aspect of the invention, the composition may include any amount of a phospholipid.

In accordance with another aspect of the invention, the composition may include any amount of glyceryl stearate. In another aspect of the invention, the composition may include any amount of stearic acid. In another aspect of the invention, the composition may include any amount of cetearyl alcohol. In another aspect of the invention, the composition may include any amount of ceteareth 20. In another aspect of the invention, the composition may include any amount of isopropyl palmitate. In another aspect of the invention, the composition may include any amount of ascorbyl polypeptide. In another aspect of the invention, the composition may include any amount of tocotrienol. In another aspect of the invention, the composition may include any amount of tocopheryl acetate. In another aspect of the invention, the composition may include any amount of ergocalciferol. In another aspect of the invention, the composition may include any amount of niacinamide. In another aspect of the invention, the composition may include any amount of ferulic acid. In another aspect of the invention, the composition may include any amount of *Camellia sinensis.* In another aspect of the invention, the composition may include any amount of *Centella asiatica.* In another aspect of the invention, the composition may include any amount of *Chamomile matricaria.* In another aspect of the invention, the composition may include any amount of *Echinacea augustifolia.*

In accordance with another aspect of the invention, the composition may include any amount of *Ginko biloba.* In another aspect of the invention, the composition may include any amount of butylene glycol. In another aspect of the invention, the composition may include any amount of phenoxyethanol. In another aspect of the invention, the composition may include any amount of caprylyl glycol. In another aspect of the invention, the composition may include any amount of sorbic acid. In another aspect of the invention, the composition may include any amount of peg8/SMDI copolymer. In another aspect of the invention, the composition may include any amount of superoxide dismutase liposomes. In another aspect of the invention, the composition may include any amount of N-acetyl carnitine. In another aspect of the invention, the composition may include any amount of alpha lipoic acid. In another aspect of the invention, the composition may include any amount of l-arginine.

In accordance with another aspect of the invention, the composition may include any amount of *Glycine soja.* In another aspect of the invention, the composition may include any amount of *Rumex crispis*. In another aspect of the invention, the composition may include any amount of *Vitis vinifera*. In another aspect of the invention, the composition may include any amount of hinokitiol. In another aspect of the invention, the composition may include any amount of retinol. In another aspect of the invention, the composition may include any amount of *Panax ginseng*. In another aspect of the invention, the composition may include any amount of allantoin. In another aspect of the invention, the composition may include any amount of kaolin. In another aspect of the invention, the composition may include any amount of bentonite. In another aspect of the invention, the composition may include any amount of *Undaria pinnatifida*. In another aspect of the invention, the composition may include any amount of diatomite silica. In another aspect of the invention, the composition may include any amount of n-acetyl glucosamine. In another aspect of the invention, the composition may include any amount of phytoplankton. In another aspect of the invention, the composition may include any amount of a member of the *Skeletonema*. In another aspect of the invention, the composition may include any amount of a member of the *Thalassiosira*. In another aspect of the invention, the composition may include any amount of a member of the *Chaetocero*. In another aspect of the invention, the composition may include any amount of *Fucus vesiculosus*. In another aspect of the invention, the composition may include any amount of sodium pCA. In another aspect of the invention, the composition may include any amount of magnesium ascorbyl phosphate. In another aspect of the invention, the composition may include any amount of epigallocatechin (EGCG). In another aspect of the invention, the composition may include any amount of ellagic acid. In another aspect of the invention, the composition may include any amount of sodium citrate. In another aspect of the invention, the composition may include any amount of tetrasodium EDTA. In another aspect of the invention, the composition may include any amount of an emollient. In another aspect of the invention, the composition may include any amount of a sunscreen. The sunscreen may be an organic sunscreen. The sunscreen may be an inorganic sunscreen. In another aspect of the invention, the composition may include any amount of a silicone surfactant. The silicone surfactant may be cyclomethicone or dimethicone copolyol.

In another aspect of the invention, the composition may include any amount of a preservative. The preservative may be methylisothiazolinone, cetylsyredinium chloride, silver, benzyl pCA, or polyaminopropyl biguamide. In another aspect of the invention, the composition may include any amount of an aqueous botanical antioxidant. The aqueous botanical antioxidant may be hydroxytyrosol, rutin, silymarin, turmeric, genistein, apple, green coffee, quercetin, or rosemary. In another aspect of the invention, the composition may include any amount of a humectant. The humectant may be a glycerol, a sorbitol, or a polyol. In another aspect of the invention, the composition may include any amount of a thickener. The thickener may be a cosmetic gum. The cosmetic gum may be alginic acid, xanthan gum, cellulose gum, hydroxtethyl cellulose, dextrin, agar, guar gum, phycocolloid, ghatti gum, cellulose ester, modified potato starch, or pectin. In another aspect of the invention, the composition may include any amount of an oligomer. The oligomer may be iso-olefin, isodecane, hydrogenated polybutene, hydrogenated polydecene, polycaprolactone, fibronectin or polyethylene glycol. In another aspect of the invention, the composition may include any amount of an amino acid. The amino acid may be present in its natural form. The amino acid may be a synthetic amino acid.

In another aspect of the invention, the composition may include any amount of a mineral and its salt. The mineral may be calcium, magnesium, manganese, or zinc. In another aspect of the invention, the composition may include any amount of a base. The base may be a soluble plant butter, a soluble plant wax, an anhydrous plant based cholesterol base, a phycocolloid gel base, a prepared polyethylene glycol ointment base, or a prepared carbomer gel base. In another aspect of the invention, the composition may include any amount of a marine component. The marine component may be an *Enteromorpha* species, a *Porphyra* species, a *Chrondus* species, a *Laminares* species, a kelp species or a *Fucals* species. In another aspect of the invention, the composition may include any amount of an anti-inflammatory agent. The anti-inflammatory agent may be *Glycyrrhiza glabria, Boswellia serrata, Curcuma longa*, turmeric, *Arnica montana*, silymarin, water melon, calendula, eidelweiss, or ginger. In another aspect of the invention, the composition may include any amount of a surfactant. The surfactant may be amphoteric. The surfactant may be cocomidopropyl betaine. The surfactant may be non-ionic. The surfactant may be cocoglucoside or coco polyglucose. The surfactant may be cationic. The surfactant may be lauryl dimoniumhydrolysed collagen.

In another aspect of the invention, the composition may include any amount of a percutaneous penetration enhancer. The percutaneous penetration enhancer may be polyethylene glycol or oleic acid. In another aspect of the invention, the composition may include any amount of a preservative enhancer. The preservative enhancer may be ethylhexyl glycerin, benzethonym chloride, or a hydantoin/PCB blend. In another aspect of the invention, the composition may include any amount of a vasodilator. The vasodilator may be adenosine triphosphate or liposomal 1 arginine. In another aspect of the invention, the composition may include any amount of a vasoconstrictor. The vasoconstrictor may be sea buckthorn, milk thistle, or marshmallow root. In another aspect of the invention, the composition may include any amount of a whitening agent. In another aspect of the invention, the composition may include any amount of a tyrosinase inhibitor. The tyrosinase inhibitor may be selected from the *Glycyrrhiza* species. The tyrosinase inhibitor may be a favnoid, a polyphenol, an isoflavone, a seaweed extract, or a coumarin. In another aspect of the invention, the composition may include any amount of octadecnedioic acid. In another aspect of the invention, the composition may include any amount of chalcones.

Other aspects and features of the present invention will become apparent to those ordinarily skilled in the art upon review of the following description of specific embodiments of the invention.

DETAILED DESCRIPTION

Any terms not directly defined herein shall be understood to have the meanings commonly associated with them as understood within the art of the invention. Certain terms are discussed below, or elsewhere in the specification, to provide additional guidance to the practitioner in describing the compositions, devices, methods and the like of embodiments of the invention, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples in the specification, including examples of terms, is for illustrative purposes only and does not limit the scope and meaning of the embodiments of the invention herein.

In accordance with one aspect of the invention there is provided a cosmetic composition for applying to skin. The composition is comprised of a liquid and dispersed in the liquid is any amount or type of fucoidan, any amount or type of beta glucan, and any amount of a marine extract. Beta glucan can be derived from a yeast extract or, for example, from a mushroom. When applied to the skin, the cosmetic composition improves the appearance of the skin. Improved appearance of the skin may be associated with any one of the following but is not limited to the following: decreased skin wrinkles, increased skin smoothness, decreased roughness of the skin, increased luminosity of the skin, increased clarity of the skin, increased firmness of the skin, increased tautness of the skin, decreased irritation of the skin, decreased skin-associated inflammation, improved skin tone, improved hydration of the skin, decreased dryness of the skin, improvements in skin discoloration, and decreased breakouts of skin conditions such as acne.

Optionally, the liquid may be water, and can include but is not limited to distilled water. Optionally, the liquid may be a glycolic acid-salicylic acid solution. Further, and optionally, the liquid may be a combination of water, including but not limited to distilled water, and a glycolic acid-salicylic acid solution. Optionally, the marine extract used in the combination may include one or more of a green seaweed, a brown seaweed, an exopolysaccharide, or an algae. A green seaweed may include but is not limited to the *Ulva* genus and particularly *Ulva lactuta*. A brown seaweed may include but is not limited to laminariales, which is commonly known as kelp and fucals. A brown seaweed may include *Ecklonia cava*. An expolysaccharide is understood to be a high-molecular-weight polymer of sugar residues. Algae may include but are not limited to members of the following groups: Archaeplastida, Rhizaria, Excavata, Excavata, Chromista, and Alveolata. Optionally, the composition may include a marine extract selected from *Ulva lactuta, Undaria pinnatifida, Fucus vesiculosus, Alteromonas maclodeii,* Astaxanthin, or *Ecklonia cava.*

Optionally, the composition may include any amount of tourmaline. Optionally, the composition may include any amount of volcanic obsidian. The composition may include any amount of *Aloe barbadensis*. The composition may further include any amount of hydrolyzed pearl nacre. Optionally, the composition may include any amount of chitosan. Optionally, the composition may include any amount of a phospholipid. A phospholipid is understood as being any of a variety of phosphorous-containing lipids that are composed mainly of fatty acids, a phosphate group, and a simple organic molecule. Optionally, the composition may include any amount of glyceryl stearate. Optionally, the composition may include any amount of stearic acid. Optionally, the composition may include any amount of cetearyl alcohol.

Further, the composition may include any amount of ceteareth 20. The composition may also include any amount of isopropyl palmitate. Optionally, the composition may include any amount of one or more of the following: ascorbyl polypeptide, tocotrienol, tocopheryl acetate, ergocalciferol, niacinamide, or ferulic acid. Optionally, the composition may include any amount of *Camellia sinensis*. Further, the composition may include any amount of one or more of the following: *Centella asiatica, Chamomile matricaria, Echinacea augustifolia,* or *Ginko biloba*. Optionally, the composition may include any amount of one or more of the following: butylene glycol, phenoxyethanol, caprylyl glycol, sorbic acid, peg8/SMDI copolymer, superoxide dismutase liposomes, N-acetyl carnitine, alpha lipoic acid, or 1-arginine.

Further, the composition may include any amount of one or more of the following: *Glycine soja, Rumex crispis, Vitis vinifera,* hinokitiol, retinol, *Panax ginseng,* allantoin, kaolin, bentonite, *Undaria pinnatifida,* diatomite silica, or n-acetyl glucosamine. The composition may further include any amount of a phytoplankton species. The composition may include any amount of a member of the *Skeletonema*. The composition may include any amount of a member of the *Thalassiosira*. The composition may include any amount of a member of the *Chaetoceros.*

Further, the composition may include any amount of *Fucus vesiculosus*. The composition may include any amount of one or more of the following: sodium pCA, magnesium ascorbyl phosphate, epigallocatechin (EGCG), ellagic acid, sodium citrate, or tetrasodium EDTA. The composition may include any amount of an emollient. An emollient is understood as being a material used for the prevention or relief of dryness, as well as for the protection of the skin.

The composition may include any amount of a sunscreen. The sunscreen may be an organic sunscreen. According to an embodiment of the invention, the composition may include from approximately 0.1 to approximately 10%, and preferably from approximately 1 to approximately 5% by weight of an organic sunscreen material. The sunscreen may be an inorganic sunscreen. According to an embodiment of the invention, the composition may include an inorganic sunscreen such as titanium dioxide or zinc oxide, having an average particle size of from 1 to 300 nm, or iron oxide, having an average particle size of from 1 to 300 nm, or silica, having an average particle size of from 1 to 100 nm.

The composition may include any amount of a silicone surfactant, which may include but is not limited to cyclomethicone or dimethicone copolyol. The composition may include any amount of a preservative. Examples of a preservative include but are not limited to methylisothiazolinone, cetylsyredinium chloride, silver, benzyl pCA, or polyaminopropyl biguamide.

Further, the composition may include any amount of an aqueous botanical antioxidant. Examples of an aqueous botanical antioxidant include, but are not limited to, hydroxytyrosol, rutin, silymarin, turmeric, genistein, apple, green coffee, quercetin, or rosemary. Further, the composition may include any amount of a humectant. The humectant may be a glycerol, a sorbitol, or a polyol. The humectant chosen is not limited to the foregoing list of humectants.

The composition may include any amount of a thickener, including but not limited to, a cosmetic gum. The cosmetic gum may include, but is not limited to, alginic acid, xanthan gum, cellulose gum, hydroxtethyl cellulose, dextrin, agar, guar gum, phycocolloid, ghatti gum, cellulose ester, modified potato starch, or pectin. Further, the composition may include any amount of an oligomer, including but not limited to, an oligomer of iso-olefin, isodecane, hydrogenated polybutene, hydrogenated polydecene, polycaprolactone, fibronectin or polyethylene glycol. An oligomer is understood as representing a few of the aforementioned monomeric units.

The composition may include any amount of an amino acid. The amino acid may be in its natural form or it may be a synthetic amino acid. An amino acid may be described as, for example, polar, non-polar, acidic, basic, aromatic or neutral. A polar amino acid is an amino acid that may interact with water by hydrogen bonding at biological or near-neutral pH. The polarity of an amino acid is an indicator of the degree of hydrogen bonding at biological or near-neutral pH. Examples of polar amino acids include serine, proline, threonine, cysteine, asparagine, glutamine, lysine, histidine, arginine, aspartate, tyrosine and glutamate. Examples of non-polar amino acids include glycine, alanine, valine leucine, isoleucine, methionine, phenylalanine, and tryptophan. Acidic amino acids have a net negative charge at a neutral pH. Examples of acidic amino acids include aspartate and glutamate. Basic amino acids have a net positive charge at a neutral pH. Examples of basic amino acids include arginine, lysine and histidine. Aromatic amino acids are generally nonpolar, and may participate in hydrophobic interactions. Examples of aromatic amino acids include phenylalanine, tyrosine and tryptophan. Tyrosine may also participate in hydrogen bonding through the hydroxyl group on the aromatic side chain. Neutral, aliphatic amino acids are generally nonpolar and hydrophobic. Examples of neutral amino acids include alanine, valine, leucine, isoleucine and methionine. An amino acid may be described by more than one descriptive category. Amino acids sharing a common descriptive category may be substitutable for each other in a peptide.

An amino acid residue may be generally represented by a one-letter or three-letter designation, corresponding to the trivial name of the amino acid, in accordance with the following Table A.

Amino acids comprising the peptides described herein will be understood to be in the L- or D-configuration. Amino acids described herein, may be modified by methylation, amidation, acetylation or substitution with other chemical groups which may change the circulating half-life of the peptide without adversely affecting their biological activity. Additionally, a disulfide linkage may be present or absent in the peptides of the invention.

Nonstandard amino acids may occur in nature, and may or may not be genetically encoded. Examples of genetically encoded nonstandard amino acids include selenocysteine, sometimes incorporated into some proteins at a UGA codon, which may normally be a stop codon, or pyrrolysine, sometimes incorporated into some proteins at a UAG codon, which may normally be a stop codon. Some nonstandard amino acids that are not genetically encoded may result from modification of standard amino acids already incorporated in a peptide, or may be metabolic intermediates or precursors, for example. Examples of nonstandard amino acids include 4-hydroxyproline, 5-hydroxylysine, 6-N-methyllysine, gamma-carboxyglutamate, desmosine, selenocysteine, ornithine, citrulline, lanthionine, 1-aminocyclopropane-1-carboxylic acid, gamma-aminobutyric acid, carnitine, sarcosine, or N-formylmethionine. Synthetic variants of standard and non-standard amino acids are also known and may include chemically derivatized amino acids, amino acids labeled for identification or tracking, or amino acids with a variety of side groups on the alpha carbon. Examples of such side groups are known in the art and may include aliphatic, single aromatic, polycyclic aromatic, heterocyclic, heteronuclear, amino, alkylamino, carboxyl, carboxamide, carboxyl ester, guanidine, amidine, hydroxyl, alkoxy, mercapto-, alkylmercapto-, or other heteroatom-containing side chains.

TABLE A

Nomenclature and abbreviations of the 20 standard L-amino acids commonly found in naturally occurring peptides

| Full name | Three-letter abbreviation | One-letter abbreviation |
| --- | --- | --- |
| Alanine | Ala | A |
| Cysteine | Cys | C |
| Aspartic acid | Asp | D |
| Glutamic acid | Glu | E |
| Phenylalanine | Phe | F |
| Glycine | Gly | G |
| Histidine | His | H |
| Isoleucine | Ile | I |
| Lysine | Lys | K |
| Leucine | Leu | L |
| Methionine | Met | M |
| Asparagine | Asp | N |
| Proline | Pro | P |
| Glutamine | Gln | Q |
| Arginine | Arg | R |
| Serine | Ser | S |
| Threonine | Thr | T |
| Valine | Val | V |
| Tryptophan | Trp | W |
| Tyrosine | Tyr | T |

Other synthetic amino acids may include alpha-amino acids, non-alpha amino acids such as beta-amino acids, des-carboxy or des-amino acids. Synthetic variants of amino acids may be synthesized using general methods known in the art, or may be purchased from commercial suppliers, for example RSP Amino Acids LLC (Shirley, Mass.).

Additionally, the composition may include any amount of a mineral and its salt. The mineral may be calcium, magnesium, manganese, or zinc. The mineral chosen is not limited to the aforementioned minerals. The composition may include any amount of a base, including but not limited to, a soluble plant butter, a soluble plant wax, an anhydrous plant based cholesterol base, a phycocolloid gel base, a prepared polyethylene glycol ointment base, or a prepared carbomer gel base. The composition may include any amount of a marine component including, but not limited to, any one or more of the following: an *Enteromorpha* species, a *Porphyra* species, a *Chrondus* species, a *Laminares* species, a kelp species or a *Fucals* species. Further, the algae utilized herein may be a brown seaweed, a red seaweed, or a green seaweed. The seaweeds may be selected based on their content of natural amino acids, fatty acids (ceramides) and their glycosyl derivatives, sterols, natural antimicrobials, ursolic acid, and moo/polysaccharides.

Further, the composition may include any amount of an anti-inflammatory agent. The anti-inflammatory agent may include, but is not limited to, any one or more of the following: *Glycyrrhiza glabria, Boswellia serrate, Curcuma longa*, turmeric, *Arnica montana*, silymarin, water melon, calendula, eidelweiss, or ginger.

The composition may include any amount of a surfactant. The surfactant may be amphoteric. They surfactant may be, but is not limited to, cocomidopropyl betaine. The surfactant may be non-ionic. The surfactant may be, but is not limited to, cocoglucoside or coco polyglucose. The surfactant may be cationic. The surfactant may be, but is not limited to, lauryl dimoniumhydrolysed collagen.

The composition may include any amount of a percutaneous penetration enhancer including, but not limited to, any one or more of the following: polyethylene glycol or oleic acid. The composition may include any amount of a preservative enhancer including, but not limited to, any one or more of the following: ethylhexyl glycerin, benzethonym chloride, or a hydantoin/PCB blend. Further, the composition may include any amount of a vasodilator including, but not limited to, any one of the following: adenosine triphosphate or liposomal 1 arginine.

Further, the composition may include any amount of a vasoconstrictor including, but not limited to, any one or more of the following: sea buckthorn, milk thistle, or marshmallow root. Additionally, the composition may include any amount of a whitening agent. The composition may include any amount of a tyrosinase inhibitor including, but not limited to, an inhibitor selected from the *Glycyrrhiza* species. The tyrosinase inhibitor may include, but is not limited to, a favnoid, a polyphenol, a seaweed extract, an isoflavone, or a coumarin. Further, the composition may include any amount of octadecnedioic acid or chalcones or a combination thereof.

Although the foregoing invention has been described in some detail by way of illustration and example for purposes of clarity of understanding, it will be readily apparent to those of skill in the art in light of teachings of this invention that changes and modification may be made thereto without departing from the spirit or scope of the invention. All patents, patent applications, and other publications referred to herein are hereby incorporated by reference.

EXAMPLES

Example 1

Composition with Acidified Fucoidan, Beta Glucan, and Ascorbyl Polypeptide

In accordance with an embodiment of the present invention, a composition is described having the components shown in Table 1 below. The methodology employed in producing the composition using the amounts described in Table 1 below is generally as follows.

Method Sequence No. 1

In a first mixture, neutralized glycolic and salicyclic acid solution (source: Spectrum Chemical; Gardena, Calif.) was heated in a stainless steel container to approximately 85 degrees Celsius. The seaweed complex consisting of *Ulva lactuta*, *Alteromonas maclodeii*, and astaxanthin (source: Unipex Innovations, Mississauga, Ontario) was added to the heated glycolic acid mixture. The combined mixture was mixed for approximately 45 to 60 minutes.

TABLE 1

Components of an embodiment of the invention

| Sequence No. | Component | Amount (% by weight) |
| --- | --- | --- |
| I | Glycolic acid-salicylic acid solution (ratio: 8:1) (neutralized with ammonium hydroxide; ammonium glycolate, sodium lactate can also be added to obtain a preferable pH of ~4) | 10 |
| I | Seaweed complex containing *Ulva lactuta*, *Alteromonas maclodeii* and Astaxanthin (ratio: 7:1.5:1.5) | 5.5 |
| I | Distilled Water | 20.8 |
| I | Tourmaline (0.15%) and volcanic obsidian (0.05%) | 0.2 |
| I | Beta glucan (yeast and specified medicinal fungi extract combined in a 1:1 ratio) and fucoidan complex (beta glucan and fucoidan are present in a 1:1 ratio) | 8 |
| I | Aqueous *Aloe barbadensis* extract | 10 |
| I | Hydrolyzed pearl nacre (1.5%) and chitosan (0.5%) | 2.5 |

TABLE 1-continued

Components of an embodiment of the invention

| Sequence No. | Component | Amount (% by weight) |
| --- | --- | --- |
| I | Phospholipids | 10 |
| II | Glyceryl stearate, stearic acid, cetearyl alcohol, ceteareth 20, isopropyl palmitate complex (each of these products is added at an equal amount) | 15 |
| II | Ascorbyl polypeptide, tocotrienol, tocopheryl acetate, ergocalciferol, niacinamide complex (ratio of these products: 3:1:1:1:1:1) | 6 |
| II | Aqueous extract of *Camellia sinensis*, *Centella asiatica*, *Chamomile matricaria*, *Echinacea augustifolia*, *Ginko biloba* (each of these products is added at an equal amount) | 1.5 |
| III | Complex of butylene glycol, phenoxyethanol, caprylyl glycol, sorbic acid, peg8/SMDI copolymer (these products are added at the following ratio: 1.5:0.5:0.25:0.25:0.25) | 2.5 |
| III | Aqueous superoxide dismutase liposomes | 8 |

A polarized water was developed by adding tourmaline and obsidian (source: Soliance; Paris, France) to the distilled water. The beta glucan (source: Biothera; Eagen, Minn.) and fucoidan (source: Marinova; Cambridge, Tasmania, Australia) complex was dissolved in one-third of the polarized water. The dissolved beta glucan-fucoidan complex was added to the glycolic acid mixture (previously described above) and the entire solution was maintained at approximately 85 degrees Celsius for approximately 30 minutes. While maintaining mixing of the mixture, aqueous *Aloe barbedensis* leaf extract (source: Tri K Industries; Northvale, N.J.) was added and the entire mixture was allowed to cool for approximately 30 minutes. Thereafter, hydrolyzed pearl nacre (source: Active Concepts; Lincolnton, N.C.) and chitosan (source: Alfa Chem; Kings Point, N.Y.) were added to the cooled mixture. The entire mixture was allowed to cool to approximately 30 degrees Celsius. Thereafter, phospholipids (source: Arch Personal Care; Norwalk, Conn.) were added to the cooled mixture.

Method Sequence No. 2

In a further mixture, glyceryl stearate, stearic acid, cetearyl alcohol, ceteareth 20, and isopropyl palmitate complex (source: Hallstar Corp.; Chicago, Ill.) were heated to 75 degrees Celsius in a 200 kg stainless steel vat. The mixture was mixed by continuous stirring for approximately 60 minutes.

Separately, the remaining two-thirds of polarized water (as described above) was used to dissolve the ascorbyl polypeptide-tocotrienol complex (source: Arch Personal Care). The ascorbyl polypeptide-tocotrienol complex was allowed to dissolve in the polarized water for approximately one hour. Thereafter, aqueous extracts of *Camellia sinensis*, *Centella asiatica*, *Chamomile matricaria*, *Echinacea augustifolia*, and *Ginko biloba* (source: Active Organics; Louisville, Tex.) were added to the ascorbyl polypeptide-tocotrienol complex.

Method Sequence No. 3

In a further mixture, butylene glycol, phenoxyethanol, caprylyl glycol, sorbic acid, and peg8/SMDI copolymer were added at the ratio described above to make a complex (source: International Specialty Products; Mississauga, Ontario). Thereafter, this complex was added to the glyceryl stearate complex mixture described above, the glyceryl stearate complex having been maintained at approximately 75 degrees Celsius. Thereafter, the ascorbyl polypeptide-tocotrienol complex, which had previously been mixed with the aqueous extracts described above, was added and agitation of the mixture continued at approximately 75 degrees Celsius. Thereafter, the entire mixture was cooled down to approximately 30 degrees Celsius.

Thereafter, the mixture developed from Method Sequence No. 1 was added to the mixture. The mixture was allowed to cool down to approximately 20 degrees Celsius and liposomal superoxide dismutase (source: Arch Personal Care) was added.

In a modification to the above, the seaweed complex can be present as 1.5% of the formulation instead of 5.5% as described in Table 1. Further, the beta glucan and fucoidan complex can be present as 12% of the formulation instead of 8% as described in Table 1.

Testing Efficacy of Example 1

To test the efficacy of the mixture described in Example 1, the mixture was used by human subjects to determine the effect on the appearance of their skin. The results routinely showed that following application of the mixture described in Example 1, the human subjects exhibited improved appearance of their skin.

Serving as an example, JT, a female under the age of 30 years of age, used the formulation defined in Example 1. Prior to using the formulation of Example 1, JT had exhibited sensitive skin and a tendency to have acne breakouts. JT also described numerous fine lines being visible in her forehead region. On day 0, JT began using an amount approximately equivalent to the size of a quarter and used approximately that amount each morning on her skin. After one week, JT described her skin as being brighter and with an improved complexion. After two weeks, JT described that the fine lines on her skin were blurred. After one month, JT described that her skin had less breakouts and was very smooth. JT identified at least the following attributes as being associated with the formulation defined in Example 1: increased smoothness and brightness of the skin, decreased lines on JT's forehead, and decreased breakouts of acne. Further, JT identified the formulation of Example 1 as being associated with decreased dryness of the skin.

Example 2

Composition with Non-Acidified Fucoidan and Beta Glucan

In accordance with a further embodiment of the present invention, a composition is described having the components shown in Table 2. The methodology employed in producing the composition using the amounts described in Table 2 is generally as follows.

Method Sequence No. 1

In a first mixture, a polarized water was developed by adding tourmaline and obsidian (source: Soliance) to the distilled water. The seaweed complex consisting of *Uva lactuta*, Astaxanthin, *Alteromonas maclodeii* (source: Unipex Innovations; Quebec City, Quebec) was dissolved into one half of the polarized water. The mixture was maintained at approximately 85 degrees Celsius. While maintaining the temperature, the mixture was stirred for approximately 45 minutes to 60 minutes. Thereafter, beta glucan (source: Biothera) and fucoidan (source: Marinova) complex were dissolved in the seaweed complex-distilled water mixture. This mixture was maintained at approximately 85 degrees Celsius and the mixture was stirred for at least approximately 30 minutes.

Thereafter, while maintaining the mixing of the mixture, the aqueous *Aloe barbedensis* leaf extract (source: Tri K Industries) was added and the entire mixture was allowed to cool for approximately 30 minutes.

Therafter, hydrolyzed pearl nacre (source: Rita Corp.; Crystal Lake, Ill.) and chitosan (source: Alfa Chem), acetyl glucosomine (source: Alfa Chem), n-acetyl carnatine (source: Alfa Chem), alpha lipoic acid (source: Alfa Chem), and 1-arginine (source: Alfa Chem) were added to the cooled mixture. The cooled mixture was further cooled to approximately 30 degrees Celsius. Thereafter, phospholipids (source: Arch Personal Care) and sodium hyaluronate (source: Tri-K Industries) were added to the mixture.

Method Sequence No. 2

In a second mixture, glyceryl stearate, stearic acid, cetearyl alcohol, ceteareth 20, isopropyl palmitate complex (all from source: Hallstar Corp.) were heated to 75 degrees Celsius in a 200 kg. stainless steel vat. The mixture was mixed by continuous stirring for approximately 60 minutes.

TABLE 2

Components of an embodiment of the invention

| Sequence No. | Component | Amount (% by weight) |
|---|---|---|
| I | Distilled water | 18.8 |
| I | Tourmaline (0.15%) and volcanic obsidian (0.05%) | 0.2 |
| I | Seaweed complex containing *Ulva lactuta*, Astaxanthin, *Alteromonas maclodeii* (ratio of these products: 7:1.5:1.5) | 10 |
| I | Beta glucan (yeast and specified medicinal fungi extract combined in a 1:1 ratio) and fucoidan complex (beta glucan and fucoidan are present in a 1:1 ratio) | 10 |
| I | Aqueous *Aloe barbedensis* leaf extract | 12 |
| I | Hydrolyzed pearl nacre and chitosan (ratio of these products: 1.5:1) | 1.5 |
| I | N-acetyl carnitine, alpha lipoic acid, and 1-arginine (ratio of these products: 1.5:1.5:0.5) | 3.5 |
| I | Phospholipids and sodium hyaluronate (ratio of these products: 4:1) | 8 |
| II | Glyceryl stearate, stearic acid, cetearyl alcohol, ceteareth 20, isopropyl palmitate complex (each of these products is added at an equal amount) | 15 |
| II | Ascorbyl polypeptide, tocotrienol, tocopheryl acetate, ergocalciferol, ferulic acid, niacinamide complex (ratio of these products: 3:1:0.5:0.5:0.5:0.5) | 5 |
| II | *Glycine soja, Rumex crispis, Vitis vinifera*, hinokitiol (beta thujaplicin) (each of these products is added at an equal amount) | 2 |
| II | Aqueous extract of *Camellia sinensis, Centella asiatica, Chamomile matricaria, Echinacea augustifolia, Ginko biloba* (each of these products is added at an equal amount) | 2.5 |
| III | Complex of butylene glycol, phenoxyethanol, caprylyl glycol, sorbic acid, peg8/SMDI copolymer (ratio of these products: 1.5:.05:0.25:0.25:0.25) | 3.5 |
| III | Aqueous superoxide dismutase liposomes | 8 |

Separately, ascorbyl polypeptide, tocotrienol, tocopheryl acetate, ergocalciferol, ferulic acid, and niacinamide (all from source: Arch Personal Care) were dissolved into the second half of the polarized water (as described above) over a period of approximately one hour. Thereafter, *Glycine soja, Rumex crispis, Vitis vinifera*, and hinokitiol (beta thujaplicin) (all from source: Active Organics); and aqueous extracts of *Camellia sinensis, Centella asiatica, Chamomile matricaria, Echinacea augustifolia*, and *Ginko biloba* (all from source: Active Organics) were added to the ascorbyl polypeptide-tocotrienol mixture.

Method Sequence No. 3

Butylene glycol, phenoxyethanol, caprylyl glycol, sorbic acid and peg8/SMDI copolymer (all from source: International Specialty Products) were combined to form a complex. Thereafter, the complex was added to the glyceryl stearate mixture described above, while the glyceryl stearate mixture was maintained at approximately 75 degrees Celsius. Thereafter, the ascorbyl polypeptide-tocotrienol mixture described above was added and agitation of the mixture continued at approximately 75 degrees Celsius. The entire mixture was then cooled to approximately 30 degrees Celsius. Thereafter, the mixture developed above in Method Sequence No. 1 was added. Thereafter, the mixture was allowed to cool to approximately 20 degrees Celsius and liposomal superoxide dismutase (source: Arch Personal Care) was added.

In a modification to the above, the seaweed complex can be present as 4% of the formulation instead of 10% as described in Table 2. Further, the beta glucan and fucoidan complex can be present as 16% of the formulation instead of 10% as described in Table 2.

Testing Efficacy of Example 2

To test the efficacy of the mixture described in Example 2, the mixture was used by human subjects to determine the effect on the appearance of their skin. The results routinely showed that the mixture described in Example 2 improved the appearance of the skin of human subjects.

Serving as an example, MJ, a female over the age of 40 years of age, used the formulation defined in Example 2. Prior to using the formulation of Example 2, MJ had exhibited under-eye skin that was puffy, sensitive and quite dry. On day 0, MJ began using an amount approximately equivalent to the size of a dime and used approximately that amount each morning and night on her skin. After one week, MJ described her under-eye skin as being less puffy. After two weeks, MJ again described her under-eye skin as being less puffy. After one month, MJ described her under-eye skin as being tighter looking and having fewer small wrinkles such that the skin appeared to be smoother in appearance. MJ identified at least the following attributes as being associated with the formulation defined in Example 2: decreased skin wrinkles; improvement in skin tone; increased skin firmness; and increased skin hydration.

Example 3

Composition with Acidified Fucoidan, Beta Glucan and Retinol

In accordance with a further embodiment of the present invention, a composition is described having the components shown in Table 3. The methodology employed in producing the composition using the amounts described in Table 3 is generally as follows.

Method Sequence No. 1

In a first mixture, neutralized glycolic and salicylic acid solution (source: Dupont or Spectrum Chemical) was heated in a stainless steel container to approximately 85 degrees Celsius. The seaweed complex consisting of *Ecklonia cava*, *Alteromonas maclodeii*, and Astaxanthin (source: Unipex Innovations) was added to the heated glycolic acid mixture. The combined mixture was mixed for approximately 45 to 60 minutes.

Polarized water was developed by adding tourmaline and obsidian (source: Soliance) to the distilled water. The beta glucan and fucoidan complex (source: Active Concepts, Marinova) was dissolved in one-third of the polarized water. The dissolved beta glucan-fucoidan complex was added to the glycolic acid mixture (previously described above) and the entire solution continued to be stirred while the temperature was maintained at approximately 85 degrees Celsius for approximately 30 minutes. While maintaining mixing of the mixture, aqueous *Aloe barbedensis* leaf extract (source: Tri K Industries) was added and the entire mixture was allowed to cool for 30 minutes. Thereafter, hydrolyzed pearl nacre (source: Rita Corp.) and chitosan (source: Alfa Chem) were added to the cooled mixture. The entire mixture

TABLE 3

Components of an embodiment of the invention

| Sequence No. | Component | Amount (% by weight) |
|---|---|---|
| I | Glycolic and salicylic acids (ratio: 8:1) (neutralized with ammonium hydroxide; ammonium glycolate, and sodium lactate can also be added to obtain a preferable pH of ~4) | 10 |
| I | Seaweed complex containing *Ecklonia cava*, *Alteromonas maclodeii* and Astaxanthin [ratio: 7:1.5:1.5] | 5.5 |
| I | Distilled water | 14.8 |
| I | Tourmaline (0.15%) and volcanic obsidian (0.5%) | 0.2 |
| I | Beta glucan (yeast and specified medicinal fungi extract combined in a 1:1 ratio) in a 1:1 ratio with fucoidan complex | 8 |
| I | Aqueous *Aloe barbedensis* leaf extract | 10 |
| I | Hydrolyzed pearl nacre (1.5%) and chitosan (1.0%) | 2.5 |
| I | Phospholipids | 10 |
| II | Glyceryl stearate, stearic acid, cetearyl alcohol, ceteareth 20, isopropyl palmitate (each of these products is added at an equal amount) | 20 |
| II | Tocotrienol, tocopheryl acetate, niacinamide, retinol complex (ratio of these products: 3:1.5:1.5:0.5) | 6 |
| II | Aqueous extract of *Vitis vinifera*, Chamomile matricaria, Echinacea augustifolia, Panax ginseng, Glycine soja, allantoin (each of these products is added at an equal amount) | 2.5 |
| III | Complex of butylene glycol, phenoxyethanol, caprylyl glycol, sorbic acid, peg8/SMDI copolymer (ratio of these products: 1.5:0.5:0.25:0.25:0.25) | 2.5 |
| III | Aqueous superoxide dismutase liposomes | 8 | was allowed to cool to approximately 30 degrees Celsius. Thereafter, phospholipids (source: Arch Personal Care) were added to the cooled mixture.

Method Sequence No. 2

In a further mixture, glyceryl stearate, stearic acid, cetearyl alcohol, ceteareth 20, and isopropyl palmitate complex (source: Hallstar Corp.) were heated to 75 degrees Celsius in a 200 kg. stainless steel vat. The mixture was mixed by continuous stirring for 60 minutes.

Separately, the remaining two-thirds of polarized water (as described above) was used to dissolve the tocotrienol-retinol complex (source: Arch Personal Care). The tocotrienol-retinol complex was allowed to dissolve in the polarized water for one hour. Thereafter, aqueous extracts of *Vitis vinifera, Chamomile matricaria, Echinacea augustifolia, Panax ginseng, Glycine soja*, and allantoin (source: Active Organics) were added to the tocotrienol-retinol complex.

Method Sequence No. 3

In a further mixture, butylene glycol, phenoxyethanol, caprylyl glycol, sorbic acid, and peg8/SMDI copolymer were combined to make a complex (source: International Specialty Products). Thereafter, this complex was added to the glyceryl stearate complex mixture described above, the glyceryl stearate complex having been maintained at 75 degrees Celsius. Thereafter, the ascorbyl polypeptide-tocotrienol complex, which had previously been mixed with the aqueous extracts described above, was added and agitation of the mixture continued at approximately 75 degrees Celsius. Thereafter, the entire mixture was cooled down to approximately 30 degrees Celsius.

Thereafter, the mixture developed from Method Sequence No. 1 was added to the mixture. The mixture was allowed to cool down to approximately 20 degrees Celsius and liposomal superoxide dismutase (source: Arch Personal Care) was added. In a modification to the above, the seaweed complex can be present as 3.5% of the formulation instead of 5.5% as described in Table 3. Further, the beta glucan and fucoidan complex can be present as 10% of the formulation instead of 8% as described in Table 3.

Testing Efficacy of Example 3

To test the efficacy of the mixture described in Example 3, the mixture was used by human subjects to determine the effect on the appearance of their skin. The results routinely showed that the mixture described in Example 3 improved the appearance of the skin of human subjects.

Serving as an example, CO, a female between the age of 30-40 years of age, used the formulation defined in Example 3. Prior to using the formulation of Example 3, CO had exhibited oily skin that was prone to acne breakouts. Further, CO described that her skin was rough, and that skin pores were visible. Further, CO described that her skin showed an appearance of acne scarring. On day 0, CO began using an amount approximately equivalent to the size of a dime and used approximately that amount each night on her skin. After one week, CO described her skin as having faded acne scarring. After two weeks, CO described that her skin appeared to be more radiant and glowing in appearance. After one month, CO described her skin as being firmer and that the acne breakouts had stopped. CO identified at least the following attributes as being associated with the formulation defined in Example 3: decreased skin wrinkles; improvement in skin tone; increased skin firmness; and increased skin hydration.

Example 4

Composition with Acidified Fucoidan and Beta Glucan

In accordance with a further embodiment of the present invention, a composition is described having the components shown in Table 4. The methodology employed in producing the composition using the amounts described in Table 4 is generally as follows.

Tourmaline and volcanic obsidian (source: Soliance) were dissolved into distilled water. *Ulva lactuta*, fucoidan (source: Marinova), beta glucan (source: Arch Personal Care) were added to above polarized water and mixture was heated to approximately 80 degrees Celsius and stirred for approximately 40 minutes.

Neutralized glycolic acid, as disclosed herein, was added to the above mixture, and stirred at approximately 80 degrees Celsius for approximately another 30 minutes. Thereafter, *Aloe barbedensis* leaf extract (source: Tri-K) and aqueous extract of *Camellia sinensis, Centella*

TABLE 4

Components of an embodiment of the invention

| Sequence No. | Component | Amount (% by weight) |
|---|---|---|
| I | Aqueous *Aloe barbedensis* leaf extract | 45 |
| I | Distilled water | 40.8 |
| I | Tourmaline, volcanic obsidian | 0.2 |

TABLE 4-continued

Components of an embodiment of the invention

| Sequence No. | Component | Amount (% by weight) |
|---|---|---|
| I | Glycolic and salicylic acids (ratio 8:1) (neutralized with ammonium hydroxide; ammonium glycolate, and sodium lactate can also be added to obtain a preferable pH of ~4) | 6 |
| I | Fucoidan, beta glucan, *Ulva lactuta* (ratio: 5:5:1.5) | 4 |
| II | Aqueous extract of *Camellia sinensis, Centella asiatica, Chamomile matricaria, Echinacea augustifolia, Ginko biloba* (these extracts are present in equal amounts) | 1.5 |
| III | Complex of butylene glycol, allantoin, phenoxyethanol, caprylyl glycol, sorbic acid (ratio: 1.5:0.5:0.25:0.25:0.25) | 2.5 |

*asiatica, Chamomile matricaria, Echinacea augustifolia,* and *Ginko biloba* (source: Active Organics) as detailed in the corresponding Table, were added and the entire mixture was stirred for approximately another 10 minutes.

At this stage any of a variety of surfactants can be incorporated to constitute an effective cleansing composition focusing on the above key ingredients.

Thereafter, butylene glycol, allantoin, phenoxyethanol, caprylyl glycol, sorbic acid (source: International Specialty Products) were added and the entire mixture was stirred for approximately another 10 minutes. The entire mixture was then cooled to room temperature.

Testing Efficacy of Example 4

To test the efficacy of the mixture described in Example 4, the mixture was used by human subjects to determine the effect on the appearance of their skin. The results routinely showed that the mixture described in Example 4 improved the appearance of the skin of human subjects.

Serving as an example, MT, a male under the age of 30 used the formulation defined in Example 4. Prior to using the formulation of Example 4, MT had exhibited slightly acnied skin that included a small amount of wrinkling. On day 0, MT began applying the formulation defined in Example 4 to his skin using a cotton pad soaked in the formulation defined in Example 4. After one week, MT described his skin as appearing clearer with a less dull appearance. After two weeks, MT described his skin as having less breakouts of acne. After one month, MT described his skin as appearing brighter, clearer, and tighter. MT identified at least the following attributes as being associated with the formulation defined in Example 4: increased skin firmness; improved skin tone, and smoother and brighter skin appearance.

Example 5

Composition with Acidified Fucoidan

In accordance with a further embodiment of the present invention, a composition is described having the components shown in Table 5. The methodology employed in producing the composition using the amounts described in Table 5 is generally as follows.

Method Sequence No. 1

In a first mixture, neutralized glycolic acid (source: Dupont or Spectrum Chemical), salicylic acid (source: Spectrum), tourmaline and volcanic obsidian (source: Soliance) was heated

TABLE 5

Components of an embodiment of the invention

| Sequence No. | Component | Amount (% by weight) |
|---|---|---|
| I | Glycolic and salicylic acids (ratio 8:1) (neutralized with ammonium hydroxide; ammonium glycolate, and sodium lactate can also be added to obtain a preferable pH of ~4) | 12.8 |
| I | Tourmaline (0.15%) and volcanic obsidian (0.5%) | 0.2 |
| I | Kaolin and bentonite (ratio of these products: 0.6:0.3) | 26 |
| I | Beta glucan (yeast and specified medicinal fungi extract combined in a 1:1 ratio) in a 1:1 ratio with fucoidan complex, *Ulva lactuta* [5:5:1.5] | 10 |
| I | *Undaria pinnatifida* | 4 |
| I | Diatomite silica, n-acetyl glucosamine, hydrolyzed pearl nacre, and chitosan (ratio of these products: 1:1:0.25:0.25) | 2.5 |
| I | Aqueous *Aloe barbedensis* leaf extract | 10 |
| I | *Echinacea augustifolia* and *Panax ginseng* (ratio of these products: 1:1) | 2 |
| II | Stearic acid, cetearyl alcohol, and ceteareth 20 complex in equal parts (each of these products is added at an equal amount) | 30 |
| III | Complex of phenoxyethanol, caprylyl glycol, sorbic acid (ratio of these products: 1.5:0.5:0.5) | 2.5 | in a stainless steel container to approximately 85 degrees Celsius. The seaweed complex consisting of *Ulva lactuta* (source: Unipex Innovations), beta glucan-fucoidan complex (source: Biothera, Marinova), and *Undaria pinnatifida* (source: Marinova) were added to the heated glycolic acid mixture. The combined mixture was agitated for approximately 30 minutes. Diatomite silica, n-acetyl glucosamine, hydrolyzed pearl nacre (source: Rita Corp.), and chitosan (source: Alfa Chem) were added to the above mixture.

Kaolin and bentonite (source: Xenex Labs; Vancouver, British Columbia] were separately mixed and added to the above mixture. While maintaining mixing of the mixture, aqueous *Aloe barbedensis* leaf extract (source: Tri K Industries), *Echinacea augustifolia*, and *Panax ginseng* (source: Active Organics) were added.

Method Sequence No. 2

Thereafter, and separately, stearic acid, cetearyl alcohol, and ceteareth 20 complex (source: Hallstar Corp.) were heated to approximately 75 degrees C., stirring for approximately 60 minutes.

Method Sequence No. 3

In a further mixture, phenoxyethanol, caprylyl glycol, and sorbic acid (source: International Specialty Products) were combined to make a complex. Thereafter, this complex was added to the stearic acid complex described above, the stearic complex having been maintained at approximately 75 degrees Celsius. Thereafter, the entire mixture was cooled down to approximately 30 degrees Celsius. Thereafter, the mixture developed from Method Sequence No. 1 (see above) was added to the mixture. The mixture was allowed to cool to approximately 20 degrees Celsius.

In a modification to the above, the beta glucan complex can be present as 12% of the formulation instead of 10% as described in Table 5. Further, the *Undaria pinnatifida* can be present at 2% instead of 4% as described in Table 5.

Testing Efficacy of Example 5

To test the efficacy of the mixture described in Example 5, the mixture was used by human subjects to determine the effect on the appearance of their skin. The results routinely showed that the mixture described in Example 5 improved the appearance of the skin of human subjects.

Serving as an example, JT, a female between the age of 30-40, used the formulation defined in Example 5. Prior to using the formulation of Example 5, JT had exhibited skin conditions that included acne and rough spots. On day 0, JT began using an amount approximately equivalent to the size of a quarter and used approximately twice that amount twice a week. After one week, JT described her skin as having fewer breakouts of acne. After two weeks, JT described her skin as being clearer. After one month, JT described her skin as appearing smoother. JT identified at least the following attributes as being associated with the formulation defined in Example 5: increased smoothness of the skin, increased luminosity of the skin, increased firmness of the skin, increased tautness of the skin, and less irritation and skin-associated inflammation.

Example 6

Serum Composition

The methodology employed in producing the non-acidified serum composition using the amounts described in Table 6 is generally as follows.

Method Sequence No. 1

Polarized water was developed by adding tourmaline and obsidian (source: Soliance) to the distilled water. The seaweed complex consisting of phytoplankton extract (source: Canadian Pacific Phytoplankton), *Fucus vesiculosus* extract (source: Xenex), *ecklonia cava* (source: JP Renew; San Francisco, Calif.) was dissolved into one-half of the distilled water, heated to approximately 85 degrees Celsius. The combined mixture was then stirred for approximately 45 minutes to 60 minutes. The beta glucan and fucoidan complex (source: Biothera, Marinova) and vegetal astaxanthin (source: Unipex Innovations) was dissolved in the seaweed complex-distilled water mixture (previously described above). The heated mixture continued to be stirred while the temperature was maintained at approximately 85 degrees Celsius for a minimum of approximately 30 minutes. The entire mixture was allowed to cool to

TABLE 6

Components of an embodiment of the invention

| Sequence No. | Component | Amount (% by weight) |
|---|---|---|
| I | Distilled water | 40.8 |
| I | Tourmaline, volcanic obsidian [1:.5] | 0.2 |
| I | Phytoplankton extract, *Fucus vesiculosus* extract, *Ecklonia cava* complex [1:1:.5:.5] | 6 |
| I | Beta glucan (yeast and specified medicinal fungi extract combined in a 1:1 ratio), fucoidan, vegetal astaxanthin complex [5:5:1.5] | 8 |
| I | Hydrolyzed pearl nacre, chitosan [1:.5] | 1.5 |
| I | Phospholipids, sodium pCA [1:.5] | 8 |
| II | Magnesium ascorbyl phosphate, tocotrienol, niacinamide, tocopheryl acetate, ergocalciferol complex [10:1:.5:.5:.5] | 25 |
| II | *Camellia sinensis*, epigallocatechin (EGCG), ellagic acid, 1-arginine [2:1:.5:.5] | 4 |
| III | Complex of butylene glycol, phenoxyethanol, caprylyl glycol, sorbic acid, peg8/SMDI copolymer [2:1:.5:.5:.5] | 3.5 |
| III | Sodium citrate, tetrasodium EDTA [1:.5] | 3 | to approximately 30 degrees Celsius. Thereafter, hydrolyzed pearl nacre (source: Active Concepts) and chitosan (source: Alfa Chem) were added to the cooled mixture. Thereafter, phospholipids (source: Arch Personal Care) and sodium hyaluronate (source: Tri-K Industries) were added to the cooled mixture.

Method Sequence No. 2:

In a further mixture, a complex comprising magnesium ascorbyl phosphate (source: Optima Specialty; Huntington, Conn.) with tocotrienol, niacinamide, tocopheryl acetate, ergocalciferol (source: Arch Personal Care) was mixed into the remaining one-half of polarized water and heated to approximately 70 degrees Celsius. This mixture was allowed to dissolve in the polarized water for one hour. Thereafter, *Camellia sinensis* (source: Active Organics), epigallocatechin (EGCG) (source: DSM Nutritional Products; Belvedere, N.J.), ellagic acid (source: DSM), and 1-arginine (source: Alpha Chem) were added to the ascorbyl polypeptide-tocotrienol complex.

Method Sequence No. 3

In a further mixture, butylene glycol, phenoxyethanol, caprylyl glycol, sorbic acid, and peg8/SMDI copolymer (source: International Specialty Products) are combined in the ratio specified in the Table 6 above to make a complex. Thereafter, this complex was added to the magnesium ascorbyl-tocotrienol mixture described above in Method Sequence No. 2, the magnesium ascorbyl-tocotrienol having been maintained at approximately 70 degrees Celsius. Thereafter sodium citrate and tetrasodium EDTA (source: Xenex) was added. The mixture was then stirred for approximately 15 minutes, while maintaining at approximately 70 degrees Celsius. Thereafter, the entire mixture was cooled down to approximately 30 degrees Celsius. Thereafter, the mixture developed from Method Sequence No. 1 was added to the mixture. The mixture was allowed to cool down to approximately 20 degrees Celsius.

In a modification to the above, the phytoplankton extract can be present as 2% of the formulation instead of 6% as described in Table 6. Further, the bet glucan complex can be present at 12% instead of 8% as described in Table 6.

Testing Efficacy of Example 6

To test the efficacy of the mixture described in Example 6, the mixture was used by human subjects to determine the effect on the appearance of their skin. The results routinely showed that the mixture described in Example 6 improved the appearance of the skin of human subjects.

Serving as an example, TK, a female over the age of 40 used the formulation defined in Example 6. Prior to using the formulation of Example 6, TK had exhibited sensitive skin conditions and her skin was sun-damaged. On day 0, TK began using an amount equivalent to the size of a dime of the formulation in Example 6 on a daily basis. After one week, TK described her skin as appearing more refreshed. After two weeks, TK described her skin as appearing less irritated or red as compared with before use of the formulation. After one month, TK described her skin as appearing clearer, and more firm with less wrinkle lines. TK identified at least the following attributes as being associated with the formulation defined in Example 6: increased smoothness (diminished appearance of wrinkles); increased luminosity; increased firmness; increased tautness; and less irritation and skin-associated inflammation.

Example 7

Effect of Formulation 7 on Human Skin

An experimental protocol (DCS-02-11) was designed to test the effect of a formulation that was similar to that detailed in Example 3 herein. The experimental protocol was carried out through Draelos Consulting Services of North Carolina. More particularly, the following formulation (referred to herein as Formulation 7; detailed in Table 7 herein) was prepared using methodology described herein.

This was a single-site investigator blinded study to evaluate, in part, the efficacy of Formulation 7 with respect to improving facial appearance. The subjects were compared to baseline to provide a historical control. Each subject applied the skin care product regimen twice daily and no other skin care products were utilized. Assessments consisted of investigator-led evaluations, subject evaluations, and photography of the face at each time point (baseline and 2 weeks). Noninvasive procedures of transepidermal water loss, corneometry, and skin elasticity were performed at each time point. Subjects were seen at the following intervals: Baseline and Week 2.

TABLE 7

Components of an embodiment of the invention (Formulation 7)

| Sequence No. | Component | Amount (% by weight) |
| --- | --- | --- |
| I | Glycolic and salicylic acids (ratio: 8:1) (neutralized with ammonium hydroxide; ammonium glycolate, and sodium lactate can also be added to obtain a preferable pH of ~4) | 10 |
| I | Seaweed complex containing *Undaria pinnatifida* and Astaxanthin [ratio: 7:5] | 5.5 |
| I | Distilled water | 14.8 |
| I | Tourmaline (0.15%) and volcanic obsidian (0.5%) | 0.2 |
| I | Beta glucan (yeast and specified medicinal fungi extract combined in a 1:1 ratio) in a 1:1 ratio with fucoidan complex | 8 |
| I | Aqueous *Aloe barbedensis* leaf extract | 10 |
| I | Hydrolyzed pearl nacre (1.5%) and chitosan (1.0%) | 2.5 |
| I | Phospholipids | 10 |
| II | Glyceryl stearate, stearic acid, cetearyl alcohol, ceteareth 20, isopropyl palmitate (each of these products is added at an equal amount) | 20 |
| II | Tocotrienol, tocopheryl acetate, niacinamide, Chrithmum maritimum complex (ratio of these products: 3:1.5:1.5:0.5) | 6 |
| II | Aqueous extract of *Vitis vinifera*, *Chamomile matricaria*, *Echinacea augustifolia*, *Panax ginseng*, *Glycine soja*, allantoin (each of these products is added at an equal amount) | 2.5 |

TABLE 7-continued

Components of an embodiment of the invention (Formulation 7)

| Sequence No. | Component | Amount (% by weight) |
|---|---|---|
| III | Complex of butylene glycol, phenoxyethanol, caprylyl glycol, sorbic acid, peg8/SMDI copolymer (ratio of these products: 1.5:0.5:0.25:0.25:0.25) | 2.5 |
| III | Aqueous superoxide dismutase liposomes | 8 |

Female subjects 30-70 years of age of all Fitzpatrick skin types with mild to moderate photoaging were chosen for this experimental protocol. Inclusion criteria for this experimental protocol were as follows:
1. Subjects must only apply the study product twice daily as directed to the entire face.
2. Subjects must be between 30 and 70 years of age.
3. Subjects must possess mild to moderate facial photoaging.
4. Subjects must have no medically relevant skin disease on the face.
5. Women of childbearing potential must be willing to use a form of birth control during the study. For the purpose of this study, the following were considered acceptable methods of birth control: oral contraceptives, Norplant®, Depo-Provera®, double barrier methods (e.g., condom and spermacide) and abstinence.
6. Subjects must provide written informed consent.

Exclusion criteria for this experimental protocol were as follows:
1. Any dermatological disorder, which in the investigator's opinion, may interfere with the accurate evaluation of the subject's facial skin.
2. Subjects who spend excessive time out in the sun.
3. Subjects who have demonstrated a previous hypersensitivity reaction to any of the ingredients of the study products.
4. Subjects who are pregnant, breast feeding, or planning a pregnancy.
5. Subjects with clinically significant unstable medical disorders.
6. Subjects who are unwilling or unable to comply with the requirements of the protocol.
7. Subjects who are using topical or OTC medications or creams to the face, including topical corticosteroids.
8. Subjects who have undergone a cosmetic surgical treatment to the face within the past year.
9. Subjects who use any prescription or non-prescription medications that might interfere with the topical study product in the opinion of the investigator.
10. Subjects who have history of a psychological illness or condition that would interfere with their ability to understand and follow the requirements of the study.
11. Subjects who have skin unsuitable for noninvasive assessment.

Experimental Analysis of Formulation 7 at 2-Week Time-Point

The following assessments were made at the 2-week time-point:

Elasticity:

A trend toward improved skin firmness was seen after 2 weeks of product use with a p value of 0.057. This is demonstrated by the decrease in skin elasticity observed from 6.39 at baseline to 5.05 after 2 weeks of product use (see: Table 8 herein). Briefly, the elasticity readings were conducted using a Dermalab Elasticity Machine. This machine uses suction to develop stress and relaxation curves that are computer analyzed to arrive at the final readings (as provided herein).

Investigator Assessment

The investigator assessed a statistically significant improvement in skin smoothness ($p=0.001$) and a statistically significant improvement in skin dryness ($p=0.002$) after 2 weeks of product use (see Tables 9A and 9B herein). The investigator assessment readings represent an ordinal scale where 0=none; 1=minimal; 2=mild; 3=moderate; and 4=severe.

Subject Assessment

Further, a trend was seen to an improvement in overall appearance ($p=0.056$) (see Tables 10A and 10B herein). The subject assessment readings represent an ordinal scale where 0=none; 1=minimal; 2=mild; 3=moderate; and 4=severe.

Transepidermal Water Loss (TEWL)

Further, there was a decrease in TEWL after 2 weeks of product use from the baseline value of 12.81 to 12.03 at week 2 (see Table 11 herein). The TEWL readings were conducted with a Dermalab Evaporimeter. The probes therein use two humidity meters at a known distance above the skin to determine the mg of water vapor lost per cm per minute.

TABLE 8

Elasticity Measurements at 2-week Time-point

| Subject No. | Baseline elasticity measurement | Week 2 elasticity measurement |
|---|---|---|
| 1 | 4.5 | 3.5 |
| 2 | 2.4 | 2.4 |
| 3 | 4.4 | 2.6 |
| 4 | 3.4 | 2.9 |
| 5 | 4.9 | 4.3 |
| 6 | 17.4 | 10.9 |
| 7 | 12.7 | 7.1 |
| 8 | 3.9 | 2.4 |
| 9 | 2.2 | 2 |
| 10 | 2 | 2 |
| 11 | 5.5 | 6.2 |
| 12 | 5.5 | 3.5 |
| 13 | 6 | 9.9 |
| 14 | 6.7 | 4.8 |
| 15 | 14.3 | 11.3 |
| Average | 6.39 | 5.05 |

TABLE 9A

Investigator Assessments at Baseline Time-point

| Subject # | Unblind | Lack of Firmness | Wrinkles | Fine Lines | Poor Skin Texture | Lack of Smoothness | Dryness | Overall Appearance |
|---|---|---|---|---|---|---|---|---|
| | | | | | Baseline | | | |
| 1 | A | 2 | 2 | 2 | 2 | 2 | 2 | 2 |
| 2 | A | 2 | 2 | 2 | 2 | 2 | 2 | 2 |
| 3 | A | 3 | 3 | 2 | 3 | 2 | 2 | 3 |
| 4 | A | 3 | 3 | 3 | 3 | 2 | 2 | 3 |
| 5 | A | 3 | 3 | 3 | 3 | 3 | 2 | 3 |
| 6 | A | 4 | 4 | 4 | 4 | 4 | 4 | 4 |
| 7 | A | 3 | 3 | 3 | 3 | 2 | 2 | 3 |
| 8 | A | 2 | 2 | 2 | 2 | 2 | 2 | 2 |
| 9 | A | 2 | 2 | 2 | 2 | 2 | 2 | 2 |
| 10 | A | 2 | 2 | 2 | 2 | 2 | 2 | 0 |
| 11 | A | 4 | 4 | 4 | 4 | 4 | 4 | 4 |
| 12 | A | 4 | 4 | 4 | 4 | 4 | 4 | 4 |
| 13 | A | 4 | 4 | 4 | 4 | 4 | 4 | 4 |
| 14 | A | 3 | 3 | 3 | 3 | 3 | 3 | 3 |
| 15 | A | 3 | 2 | 2 | 3 | 3 | 3 | 3 |
| Mann-Whitney two tailed paired | Mean A Baseline A A v. Baseline p = Z-score = | 2.93 | 2.87 | 2.80 | 2.93 | 2.73 | 2.67 | 2.80 |

TABLE 9B

Investigator Assessments at 2-Week Time-point

| Subject # | Unblind | Lack of Firmness | Wrinkles | Fine Lines | Poor Skin Texture | Lack of Smoothness | Dryness | Overall Appearance |
|---|---|---|---|---|---|---|---|---|
| | | | | | Week 2 | | | |
| 1 | A | 1 | 2 | 2 | 2 | 1 | 1 | 2 |
| 2 | A | 2 | 2 | 2 | 1 | 1 | 1 | 2 |
| 3 | A | 3 | 3 | 2 | 3 | 1 | 1 | 2 |
| 4 | A | 3 | 3 | 3 | 3 | 1 | 1 | 2 |
| 5 | A | 3 | 3 | 3 | 3 | 2 | 2 | 3 |
| 6 | A | 4 | 4 | 4 | 4 | 3 | 3 | 4 |
| 7 | A | 2 | 1 | 1 | 2 | 1 | 1 | 2 |
| 8 | A | 2 | 2 | 2 | 2 | 1 | 1 | 2 |
| 9 | A | 2 | 2 | 2 | 2 | 1 | 1 | 2 |
| 10 | A | 2 | 2 | 1 | 1 | 1 | 1 | 2 |
| 11 | A | 4 | 4 | 4 | 4 | 2 | 2 | 4 |
| 12 | A | 4 | 4 | 4 | 4 | 2 | 2 | 4 |
| 13 | A | 4 | 4 | 4 | 4 | 2 | 2 | 4 |
| 14 | A | 3 | 3 | 3 | 3 | 2 | 2 | 3 |
| 15 | A | 3 | 2 | 2 | 3 | 3 | 3 | 3 |
| Mann-Whitney two tailed paired | Mean A Baseline A A v. Baseline p = Z-score = | 2.80 2.93 0.727 −0.35 | 2.73 2.87 0.710 −0.37 | 2.60 2.80 0.584 −0.55 | 2.73 2.93 0.648 −0.46 | 1.60 2.73 0.001 −3.21 | 1.60 2.67 0.002 −3.09 | 2.73 2.80 0.584 −0.55 |

TABLE 10A

Subject Assessments at Baseline Time-point

| Subject # | Unblind | Lack of Firmness | Wrinkles | Fine Lines | Poor Skin Texture | Lack of Smoothness | Dryness | Overall Appearance |
|---|---|---|---|---|---|---|---|---|
| | | | | | Baseline | | | |
| 1 | A | 0 | 0 | 0 | 2 | 3 | 4 | 3 |
| 2 | A | 3 | 1 | 1 | 3 | 3 | 4 | 3 |
| 3 | A | 3 | 3 | 3 | 2 | 2 | 2 | 2 |
| 4 | A | 2 | 2 | 2 | 3 | 3 | 2 | 1 |

TABLE 10A-continued

Subject Assessments at Baseline Time-point

| | | Baseline | | | | | | |
|---|---|---|---|---|---|---|---|---|
| Subject # | Unblind | Lack of Firmness | Wrinkles | Fine Lines | Poor Skin Texture | Lack of Smoothness | Dryness | Overall Appearance |
| 5 | A | 1 | 3 | 3 | 3 | 3 | 3 | 3 |
| 6 | A | 2 | 2 | 2 | 2 | 2 | 3 | 3 |
| 7 | A | 2 | 1 | 1 | 3 | 1 | 2 | 3 |
| 8 | A | 1 | 1 | 2 | 1 | 2 | 2 | 1 |
| 9 | A | 2 | 0 | 0 | 3 | 3 | 1 | 1 |
| 10 | A | 1 | 1 | 1 | 0 | 0 | 1 | 1 |
| 11 | A | 2 | 2 | 2 | 1 | 1 | 2 | 2 |
| 12 | A | 2 | 3 | 3 | 3 | 3 | 2 | 3 |
| 13 | A | 1 | 2 | 2 | 2 | 2 | 1 | 2 |
| 14 | A | 3 | 2 | 3 | 3 | 3 | 0 | 3 |
| 15 | A | 2 | 3 | 3 | 3 | 2 | 3 | 3 |
| Mann-Whitney two tailed paired | Mean A Baseline A A v. Baseline p = Z-score = | 1.80 | 1.73 | 1.87 | 2.27 | 2.20 | 2.13 | 2.27 |

TABLE 10B

Subject Assessments at 2-Week Time-point

| | | Week 2 | | | | | | |
|---|---|---|---|---|---|---|---|---|
| Subject # | Unblind | Lack of Firmness | Wrinkles | Fine Lines | Poor Skin Texture | Lack of Smoothness | Dryness | Overall Appearance |
| 1 | A | 0 | 0 | 0 | 0 | 1 | 3 | 1 |
| 2 | A | 2 | 1 | 2 | 3 | 3 | 3 | 2 |
| 3 | A | 3 | 3 | 3 | 3 | 2 | 2 | 3 |
| 4 | A | 2 | 2 | 2 | 1 | 1 | 1 | 1 |
| 5 | A | 2 | 2 | 2 | 2 | 2 | 2 | 2 |
| 6 | A | 3 | 3 | 3 | 3 | 2 | 2 | 2 |
| 7 | A | 2 | 1 | 1 | 3 | 3 | 0 | 3 |
| 8 | A | 1 | 0 | 0 | 0 | 1 | 2 | 1 |
| 9 | A | 2 | 0 | 1 | 0 | 2 | 1 | 1 |
| 10 | A | 0 | 1 | 1 | 1 | 1 | 1 | 1 |
| 11 | A | 2 | 3 | 3 | 3 | 3 | 2 | 2 |
| 12 | A | 1 | 1 | 1 | 0 | 1 | 1 | 1 |
| 13 | A | 1 | 2 | 2 | 2 | 2 | 0 | 1 |
| 14 | A | 2 | 2 | 3 | 3 | 2 | 0 | 2 |
| 15 | A | 0 | 1 | 1 | 3 | 3 | 2 | 2 |
| Mann-Whitney two tailed paired | Mean A Baseline A A v. Baseline p = Z-score = | 1.53 1.80 0.495 −0.68 | 1.47 1.73 0.479 −0.71 | 1.67 1.87 0.576 −0.56 | 1.80 2.27 0.386 −0.87 | 1.93 2.20 0.303 −1.03 | 1.47 2.13 0.120 −1.56 | 1.67 2.27 0.056 −1.91 |

TABLE 11

Transepidermal Water Loss (TEWL) Measurements at 2-week Time-point

| Subject No. | Baseline TEWL measurement | Week 2 TEWL measurement |
|---|---|---|
| 1 | 18.2 | 11.5 |
| 2 | 13.7 | 5.7 |
| 3 | 14.4 | 13.5 |
| 4 | 12.2 | 13.3 |
| 5 | 15.8 | 13.2 |
| 6 | 5.5 | 11.1 |
| 7 | 12.3 | 5 |
| 8 | 8.9 | 7.9 |
| 9 | 8.4 | 33.3 |
| 10 | 10.7 | 9.3 |
| 11 | 10.2 | 3.1 |
| 12 | 16.1 | 7.9 |
| 13 | 16.5 | 18.9 |
| 14 | 16.2 | 15 |
| 15 | 13.1 | 11.8 |
| Average | 12.81 | 12.03 |

Example 8

Gene Chip Experiments

To examine the effect of formulations described herein on differential gene expression, gene chip experiments were conducted through the KU Genomic Facility (Lawrence, Kans.). Briefly, SH-SY5Y neuroblastoma cells were cultured for 48 hours, and then treated with 1) Formulation 9 (1% *Undaria pinnatifida* based fucoidan extract-beta glucan combination (1:1 ratio) dissolved in water; 2) water (neg. ctrl for #1); 3) Formulation 9 dissolved in 20% glycolic acid; and 4) 20% glycolic acid (neg. ctrl for #3). The treatments lasted for 12 hours, after which total RNA was extracted from the treated cells. The RNA samples were then used to hybridize to the Human Genome U133 2.0 GeneChip from Affymetrix, which is designed to interrogate all currently known human genes. After hybridization, the GeneChips were scanned and GeneChip data generated. After a series of bioinformatics analyses, genes showing significant changes (treatment #1 compared to #2; also #3 to #4) after the extract treatments were identified. A subset of these genes, that are known to be related to skin function, were identified as shown in Table 12 herein.

While specific embodiments of the invention have been described, such embodiments should be considered illustrative of the invention only and not as limiting the invention as construed in accordance with the accompanying claims.

TABLE 12

Skin-related Genes Upregulated at 12 Hour Timepoint

| Gene Symbol | Gene Name | Fold Change | Function |
|---|---|---|---|
| Formulation 9 in Glycolic Acid | | | |
| Col18A1 | collagen, type XVIII, alpha 1 | 8.91 | collagen and collagen fibril organization |
| ADAM11 | ADAM metallopeptidase domain 11 | 6.33 | metallopeptidase activity |
| ADAMTS1 | ADAM metallopeptidase with thrombospondin type 1 motif, 1 | 4.8 | metallopeptidase activity |
| CEP57 | centrosomal protein 57 kDa | 4.44 | fibroblast growth factor receptor signaling pathway |
| EGFR | epidermal growth factor receptor | 4.39 | epidermal growth factor receptor signaling pathway |
| Formulation 9 in Water | | | |
| GDF15 | growth differentiation factor 15 | 3.07 | growth factor activity |
| CEBPB | CCAAT/enhancer binding protein (C/EBP), beta | 2.22 | immune response |
| LUM | lumican | 1.82 | proteinaceous extracellular matrix |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A cosmetic composition for applying to skin, the composition comprising:
   from 1.5 wt. % to 5.5 wt. % of a seaweed complex consisting essentially of *Ulva lactuca, Alteromonas macleodii* and Astaxanthin in a ratio of about 7:1.5:1.5;
   0.15 wt. % tourmaline;
   0.05 wt. % volcanic obsidian;
   from 8 wt. % to 12 wt. % of a 1:1 13-glucan:fucoidan complex, said 13-glucan
   consisting of a 1:1 ratio of yeast 13-glucan and fungi 13-glucan; 10 wt. % of aqueous *Aloe barbadensis* leaf extract; 1.5 wt. % hydrolyzed pearl nacre; 1.0 wt. % chitosan;
   10 wt. % phospholipids;
   3 wt. % glyceryl stearate;
   3 wt. % stearic acid;
   3 wt. % cetearyl alcohol;
   3 wt. % ceteareth 20;
   3 wt. % isopropyl palmitate;
   6 wt. % of a 3:1:1:1:1 mixture of ascorbyl polypeptide, tocotrienol, tocopheryl acetate, ergocalciferol, and niacinamide;
   1.5 wt. % of a 1:1:1:1:1 mixture of the aqueous extracts of *Camellia sinensis, Centella asiatica, Matricaria chamomilla, Echinacea angustifolia*, and *Ginkgo biloba;*
   2.5 wt. % of a 1.5:0.5:0.25:0.25:0.25 complex of butylene glycol, phenoxyethanol, caprylyl glycol, sorbic acid, and PEG8/SMDI copolymer; 8 wt. % of aqueous superoxide dismutase liposomes; 20.8 wt. % purified water; and
   10 wt. % of a glycolic acid-salicylic acid solution neutralized with ammonium hydroxide, ammonium glycolate or sodium lactate,
   wherein the pH of the cosmetic composition is about 4.

2. The composition of claim 1, further comprising a sunscreen.

3. The composition of claim 1, further comprising a silicone surfactant.

4. The composition of claim 1, further comprising a preservative.

5. The composition of claim 1, further comprising a botanical antioxidant.

6. The composition of claim 1, further comprising an amino acid.

7. The composition of claim 1, further comprising a percutaneous penetration enhancer.

8. A cosmetic composition for applying to skin, the composition comprising:
   from 3.5 wt. % to 5.5 wt. % of a seaweed complex consisting essentially of *Ecklonia cava, Alteromonas macleodii* and Astaxanthin in a ratio of about 7:1.5:1.5;
   0.15 wt. % tourmaline;
   0.05 wt. % volcanic obsidian;
   from about 8 wt. % to about 10 wt. % of a 1:1 13-glucan:fucoidan complex, said 13-glucan
   consisting of a 1:1 ratio of yeast 13-glucan and fungi 13-glucan; 10 wt. % of aqueous *Aloe barbadensis* leaf extract; 1.5 wt. % hydrolyzed pearl nacre; 1.0 wt. % chitosan;
   10 wt. % phospholipids;
   4 wt. % glyceryl stearate;
   4 wt. % stearic acid;
   4 wt. % cetearyl alcohol;
   4 wt. % ceteareth 20;
   4 wt. % isopropyl palmitate;

6 wt. % of a 3:1.5:1.5:0.5 mixture of tocotrienol, tocopheryl acetate, niacinamide, and retinol;

2.5 wt. % of a 1:1:1:1:1:1 mixture of the aqueous extracts of *Vitis vinifera, Matricaria chamomilla, Echinacea angustifolia, Panax ginseng*, and *Glycine soja*, and allantoin;

2.5 wt. % of a 1.5:0.5:0.25:0.25:0.25 complex of butylene glycol, phenoxyethanol, caprylyl glycol, sorbic acid, and PEG8/SMDI copolymer; 8 wt. % of aqueous superoxide dismutase liposomes; 14.8 wt. % purified water; and 10 wt. % of a glycolic acid-salicylic acid solution neutralized with ammonium hydroxide, ammonium glycolate or sodium lactate, wherein the pH of the cosmetic composition is about 4.

9. The composition of claim 8, further comprising a sunscreen.

10. The composition of claim 8, further comprising a silicone surfactant.

11. The composition of claim 8, further comprising a preservative.

12. The composition of claim 8, further comprising a botanical antioxidant.

13. The composition of claim 8, further comprising an amino acid.

14. The composition of claim 8, further comprising a percutaneous penetration enhancer.

15. A cosmetic composition for applying to skin, the composition comprising:
   5.5 wt. % of a seaweed complex consisting essentially of *Undaria pinnatifida* and Astaxanthin in a ratio of about 7:5;
   0.15 wt. % tourmaline;
   0.05 wt. % volcanic obsidian;
   8 wt. % of a 1:1-glucan:fucoidan complex, said β-glucan consisting of a 1:1 ratio of yeast β-glucan and fungi β-glucan;
   10 wt. % of aqueous *Aloe barbadensis* leaf extract;
   1.5 wt. % hydrolyzed pearl nacre;
   1.0 wt. % chitosan;
   10 wt. % phospholipids;
   4 wt. % glyceryl stearate;
   4 wt. % stearic acid;
   4 wt. % cetearyl alcohol;
   4 wt. % ceteareth 20;
   4 wt. % isopropyl palmitate;
   6 wt. % of a 3:1.5:1.5:0.5 mixture of tocotrienol, tocopheryl acetate, niacinamide, and *crithmum maritimum;*
   2.5 wt. % of a 1:1:1:1:1:1 mixture of the aqueous extracts of *Vitis vinifera, Matricaria chamomilla, Echinacea angustifolia, Panax ginseng*, and *Glycine soja*, and allantoin;
   2.5 wt. % of a 1.5:0.5:0.25:0.25:0.25 complex of butylene glycol, phenoxyethanol, caprylyl glycol, sorbic acid, and PEG8/SMDI copolymer;
   8 wt. % of aqueous superoxide dismutase liposomes;
   14.8 wt. % purified water; and
   10 wt. % of a glycolic acid-salicylic acid solution neutralized with ammonium hydroxide, ammonium glycolate or sodium lactate,
   wherein the pH of the cosmetic composition is about 4.

16. The composition of claim 15, further comprising a sunscreen.

17. The composition of claim 15, further comprising a silicone surfactant.

18. The composition of claim 15, further comprising a preservative.

19. The composition of claim 15, further comprising a botanical antioxidant.

20. The composition of claim 15, further comprising an amino acid.

21. The composition of claim 15, further comprising a percutaneous penetration enhancer.

* * * * *